United States Patent
Hosoi

(10) Patent No.: US 7,073,907 B2
(45) Date of Patent: Jul. 11, 2006

(54) OPTOMETRIC APPARATUS

(75) Inventor: Yoshinobu Hosoi, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 356 days.

(21) Appl. No.: 10/763,437

(22) Filed: Jan. 26, 2004

(65) Prior Publication Data

US 2004/0207812 A1 Oct. 21, 2004

(30) Foreign Application Priority Data

Jan. 29, 2003 (JP) .............................. 2003-019631

(51) Int. Cl.
*A61B 3/14* (2006.01)

(52) U.S. Cl. ..................................... 351/205

(58) Field of Classification Search ................ 351/201, 351/205, 208, 211, 212
See application file for complete search history.

(56) References Cited

U.S. PATENT DOCUMENTS

| | | | | |
|---|---|---|---|---|
| 2,063,015 A | * | 12/1936 | Ames, Jr. .................... | 351/202 |
| 2,081,969 A | * | 6/1937 | Clile et al. .................. | 351/243 |
| 2,290,864 A | * | 7/1942 | Church ........................ | 356/16 |
| 3,536,384 A | * | 10/1970 | Cocks ......................... | 351/212 |
| 3,664,730 A | * | 5/1972 | Hernando .................... | 351/221 |
| 3,904,280 A | | 9/1975 | Tate, Jr. | |
| 5,463,430 A | | 10/1995 | Isogai et al. | |

FOREIGN PATENT DOCUMENTS

| | | |
|---|---|---|
| JP | A 02-052631 | 2/1990 |
| JP | A 2-52631 | 2/1990 |
| JP | A 05-168595 | 7/1993 |
| JP | A 06-181888 | 7/1994 |
| JP | A 6-181888 | 7/1994 |

* cited by examiner

*Primary Examiner*—Eric F. Winakur
*Assistant Examiner*—Theodore Shih
(74) *Attorney, Agent, or Firm*—Oliff & Berridge, PLC

(57) ABSTRACT

An optometric apparatus for subjectively examining visual functions of an eye (PE) of an examinee is disclosed. This apparatus includes: a disposing unit (2) for disposing an optical element (4) in front of the examinee's eye; a cornea position alignment optical system (20) for checking a vertex distance between a back surface of the disposed optical element and a corneal vertex of the examinee's eye; wherein the alignment optical system includes an aligning scale plate (23) provided with a scale (S1–S5) for checking the vertex distance, a reticle plate (24) provided with a reticle (24a) and placed in a different place from the aligning scale plate, and a first reference mark (30) and a second reference mark (31) for positioning an eye (OE) of an examiner in a point at a predetermined distance from the reticle plate, the first and second reference marks being provided in different places and appearing, to the examiner's eye, to have a predetermined positional relation with each other when the examiner's eye is positioned in the point at the predetermined distance from the reticle plate.

7 Claims, 8 Drawing Sheets

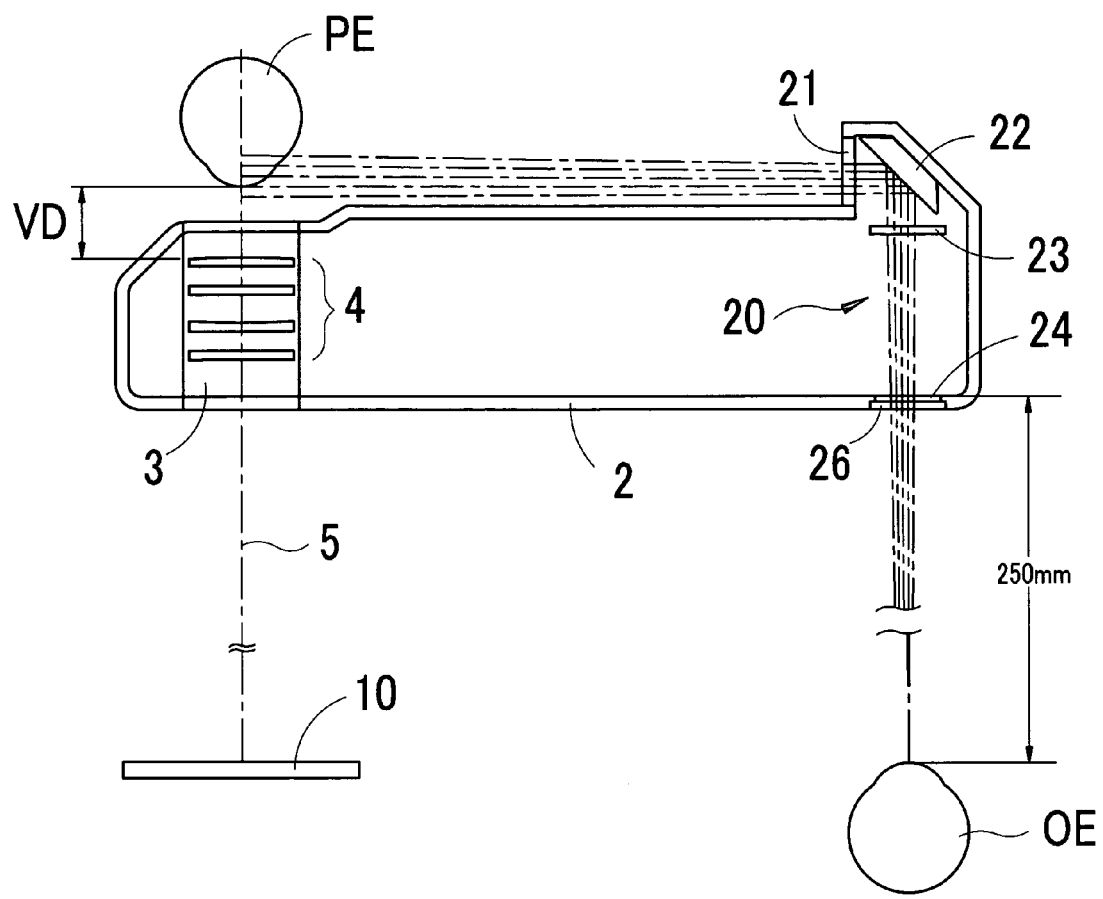

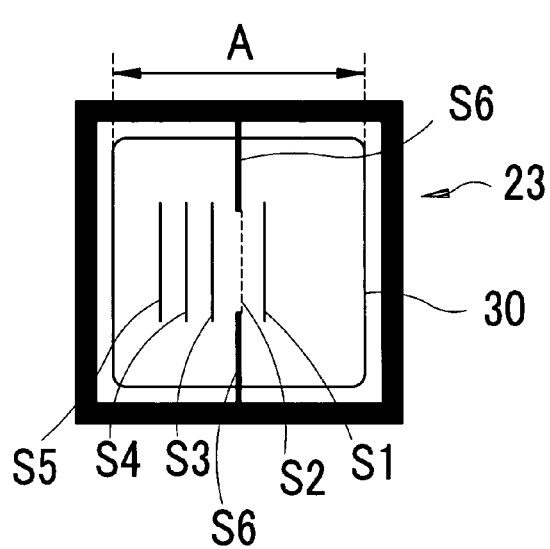 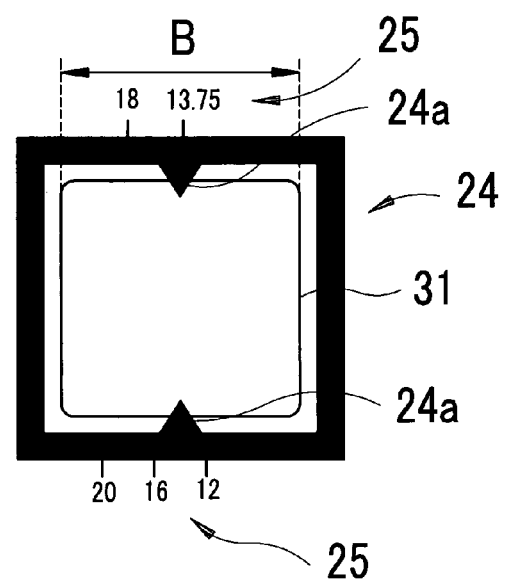

OPTOMETRIC APPARATUS

BACKGROUND OF THE INVENTION

1. Field of the Invention

The present invention relates to an optometric apparatus for subjectively examining visual functions of an examinee's eye.

2. Description of Related Art

A vertex distance VD (visual distance) between a back surface of a lens of spectacles which an examinee puts on (namely, a lens wearing reference point) and a corneal vertex of an examinee's eye is generally considered to be 13.75 mm or 12.00 mm in a reference distance. Accordingly, in an optometric apparatus adapted such that various kinds of optical elements are selectively disposed in a test window to present various kinds of optotypes through the test window in order to subjective examination of visual functions such as a refracting power of the examinee's eye and the like, the vertex distance VD between the lens (optical element) back surface and the corneal vertex needs to be checked. Thus, this type of optometric apparatus is provided with a cornea position alignment optical system for allowing check of the vertex distance VD.

FIG. 8 is a schematic sectional view of the cornea position alignment optical system provided in a conventional optometric apparatus. Various kinds of optical elements 104 are selectively disposed in a test window 103 of a lens chamber unit 100, so that the examinee's eye PE is allowed to look at an optotype 110 forward presented through the optical element 104. The lens chamber unit 100 is attached (or is separately provided) with an aligning unit 125 in which a cornea position alignment optical system 120 is mounted. This alignment optical system 120 is constructed of an aligning scale plate 121 placed to be positioned at the side of the eye PE during examinations, a reflection mirror 122, and a reticle plate 123 placed on an optical path in a direction that the mirror 122 reflects light. An examiner takes his position at a distance of 250 mm from the reticle plate 123 and then goes into position so that triangular reticles 124 provided on the reticle plate 123 appears visually aligned with a long scale line S1 provided on the aligning scale plate 121, as shown in FIG. 9. Then, the examiner checks the positional relation of the long line S1 and a plurality of short scale lines S2, formed on both sides of the long line S1, with respect to the corneal vertex. For example, if the corneal vertex appears to coincide with the long line S1, the vertex distance VD is a reference distance of 13.75 mm. The short lines S2 are spaced at intervals corresponding to several vertex distances. According to which short line S2 (or long line S1) the corneal vertex coincides with, the vertex distance VD can be checked (determined). One example of the optometric apparatus provided with the cornea position aligning system of the above type is disclosed in for example Japanese patent unexamined publication No. Hei 6-181888.

In the above mentioned cornea position aligning system, however, an eye OE of the examiner has to be substantially accurately positioned in a place 250 mm apart from the reticle plate 123; otherwise, the checked vertex distance VD would include considerable errors. If the vertex distance VD is incorrect, the results of the refractive power examination or the like would also have errors.

SUMMARY OF THE INVENTION

The present invention has been made in view of the above circumstances and has an object to overcome the above problems and to provide an optometric apparatus which allows accurate and easy check of a position of an examinee's eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optometric apparatus for subjectively examining visual functions of an eye of an examinee, the apparatus including: a disposing unit for disposing an optical element in front of the examinee's eye; a cornea position alignment optical system for checking a vertex distance between a back surface of the disposed optical element and a corneal vertex of the examinee's eye; wherein the alignment optical system includes an aligning scale plate provided with a scale for checking the vertex distance, a reticle plate provided with a reticle and placed in a different place from the aligning scale plate, and a first reference mark and a second reference mark for positioning an eye of an examiner in a point at a predetermined distance from the reticle plate, the first and second reference marks being provided in different places and appearing, to the examiner's eye, to have a predetermined positional relation with each other when the examiner's eye is positioned in the point at the predetermined distance from the reticle plate.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 1 is a schematic sectional view of an optometric apparatus in a first embodiment according to the present invention;

FIGS. 2A and 2B are schematic structural views of an aligning scale plate and a reticle plate;

DETAILED DESCRIPTION OF THE PREFERRED EMBODIMENTS

Figure 3:
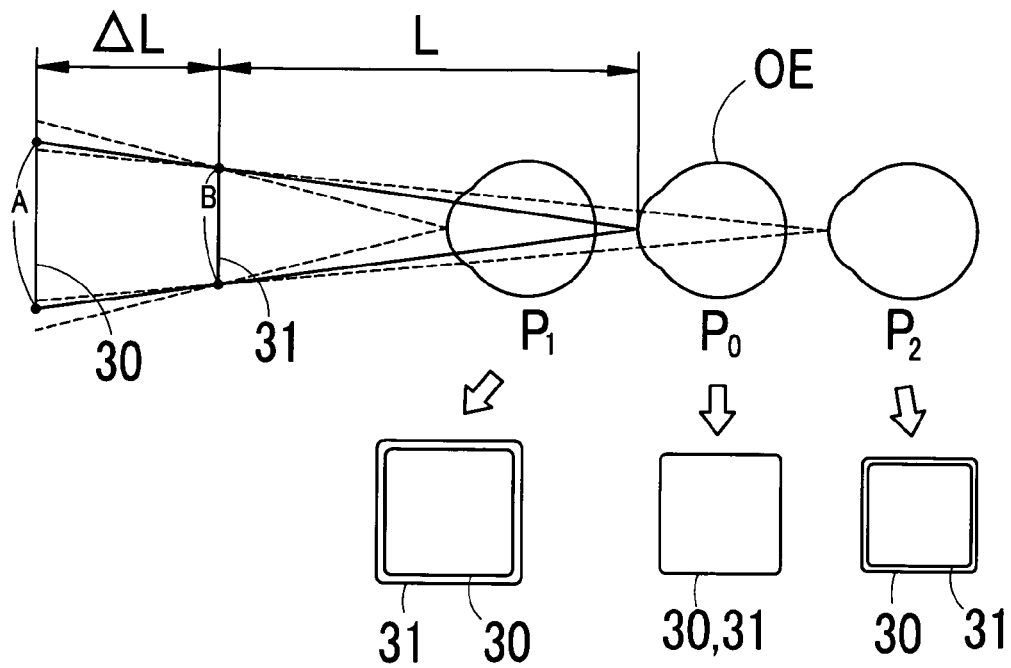
FIG. 3 is a view to explain a positional relation between a first reference mark and a second reference mark for positioning an examinee's eye in a point at a predetermined distance from a reticle plate.

A detailed description of preferred embodiments of an optometric apparatus embodying the present invention will now be given referring to the accompanying drawings. FIG. 1 is a schematic sectional view of the optometric apparatus in a first embodiment. The optometric apparatus is provided with a pair of lens chamber units for examinations of a right and left eyes of an examinee. The lens chamber units are supported by a support unit not shown so that a test window 3 is adjusted to the height of an examinee's eye PE. It is to be noted that FIG. 1 shows only a lens chamber unit 2 for a left eye examination (the eye PE is a left eye) and that a lens chamber unit for a right eye examination is simply symmetrically structured with respect to the left unit 2, and thus its detailed explanation is omitted. The right and left lens chamber units are supported by the support unit not shown so that an interval (distance) therebetween is adjustable in accordance with a pupillary distance between both eyes of the examinee.

In the lens chamber unit 2, there are provided a plurality of optical elements 4 such as a spherical lens, a cylindrical lens to be used in a refractive power examination, and so on, are selectively disposed in the test window 3. The optical elements 4 are arranged (held) in rotary disks (not shown). By rotation of the rotary disks, a desired one of the optical elements 4 can be disposed in the test window 3.

An examiner instructs the examinee to look at an examination optotype 10 presented forward of the eye PE through the optical element 4 disposed in the test window 3, the optotype 10 being placed on an examination optical axis 5. The examiner changes the optical element 4 according to how the optotype 10 visually appears. Thus, the refractive power of the eye PE can be examined.

In the lens chamber unit 2, furthermore, a cornea position alignment optical system 20 for determining a vertex distance VD between the back surface (facing the eye PE) of the optical element 4 (closest to the eye PE) and the corneal vertex of the eye PE. The alignment optical system 20 includes a reflection mirror 22 to be positioned at the side of the eye PE, an aligning scale plate 23 placed on an optical path in a direction that the mirror 22 reflects light, and a reticle plate 24. This reticle plate 24 is mounted in an observation window 26 formed in the lens chamber unit 2 at the front side (which faces the examiner). The examiner's eye OE being positioned at the front side of the lens chamber unit 2 can see the side of the eye PE through the mirror 22, the aligning scale plate 23, and the reticle plate 24. The lens chamber unit 2 further includes a window 21 to be placed between the eye PE and the mirror 22. It is to be noted that the aligning scale plate 23 may be placed in the window 21 or between the window 21 and the mirror 22 as in the conventional example. The alignment optical system 20 may also be provided in another unit, different from the lens chamber unit 2, as in the conventional example.

FIG. 2A is a schematic structural view of the aligning scale plate 23 and FIG. 2B is a schematic structural view of the reticle plate 24. The scale plate 23 is marked with several thin lines S1 to S5 as a scale. The scale lines S1, S2, S3, S4, and S5 correspond to the vertex distances of 12 mm, 13.75 mm, 16 mm, 18 mm, and 20 mm, respectively. The scale line S2 representing 13.75 mm which is a reference distance is drawn by a dotted line in order to distinguish it from other scale lines (solid lines). Two thick lines centrally-located and extended from above and below respectively are reference lines S6 for alignment in a horizontal direction. The aligning scale plate 23 is further marked with a first reference mark (target) 30. This first reference mark 30 is used to allow the examiner to adjust the position of his own eye OE to a point at a predetermined distance from the reticle plate 24, and it is formed of a rectangular frame line in the present embodiment.

The reticle plate 24 includes a black-colored peripheral portion and a transparent inside portion. The reticle plate 24 is formed with two triangular reticles 24a of which respective apexes face each other on a center line of the reticle plate 24. The reticle plate 24 is also provided with a second reference mark (target) 31. This reference mark 31, which is used in combination with the first reference mark 30 of the aligning scale plate 23, is formed of a rectangular frame line like the first reference mark 30. The reticle plate 24 is also formed with numerical indices 25 representing vertex distances VD in the black-colored peripheral portion.

It is to be noted that the aligning scale plate 23, the scale lines S1 to S5, the reference lines S6, and the reticle plate 24 and the reticles 24a may be changed variously in shape and size.

FIG. 3 is a view to explain a positional relation between the first reference mark 30 and the second reference mark 31 in order to allow the examiner to adjust the position of his eye OE to a point at a predetermined distance from the reticle plate 24. The sizes A and B of the first and second reference marks 30 and 31 are determined so that the marks 30 and 31 appear overlapped when the eye OE is positioned at a distance L of 250 mm from the reticle plate 24. In other words, assuming that the size of the first reference mark 30 is "A", the size of the second reference mark 31 is "B", the design distance between the second reference mark 31 of the reticle plate 24 and the position at which the eye OE is to be positioned is "L (250 mm)", and the distance between the first and second reference marks 30 and 31 is "ΔL", the sizes A and B are determined so that the following relation is established:

$$L/(L+\Delta L)=B/A$$

In the case where the eye OE is positioned in a point P1 at a shorter distance than the distance L (250 mm), the first reference mark 30 will appear positioned inside the second reference mark 31. On the other hand, in the case where the eye OE is positioned in a point P2 at a longer distance than the distance L (250 mm), the first reference mark 30 will appear positioned outside the second reference mark 31. Accordingly, if the position of the eye OE is adjusted so that the first and second reference marks 30 and 31 appear overlapped as a single mark, the examiner can accurately position his eye OE in a point P0 just at the distance L (250 mm).

In the present embodiment, both the first and second reference marks 30 and 31 are provided as a rectangular frame line, so that vertical and horizontal alignment of these marks 30 and 31 allows the examiner to easily adjust his eye OE in a vertical and horizontal directions. The marks 30 and 31 may be formed of a circular frame line, a straight line, or a dot; that is, their shapes, line styles, etc. may be modified or changed variously. Furthermore, the marks 30 and 31 may have different colors to further improve their visibility. It is to be noted that the marks 30 and 31 may be provided anyplace on the optical path of the alignment optical system 20, not limited to the aligning scale plate 23 and the reticle plate 24.

To check the position of the corneal vertex (i.e., the vertex distance VD) of the eye PE, the examiner adjusts the position of his own eye OE while peeping through the observation window 26 to look at the reticle plate 24, until the second reference mark 31 of the reticle plate 24 appears overlapped, as a single mark, with the first reference mark 30 of the aligning scale plate 23. In this manner, the examiner can easily adjust his eye OE to a point at a distance L of 250 mm from the reticle plate 24.

Figure 4:
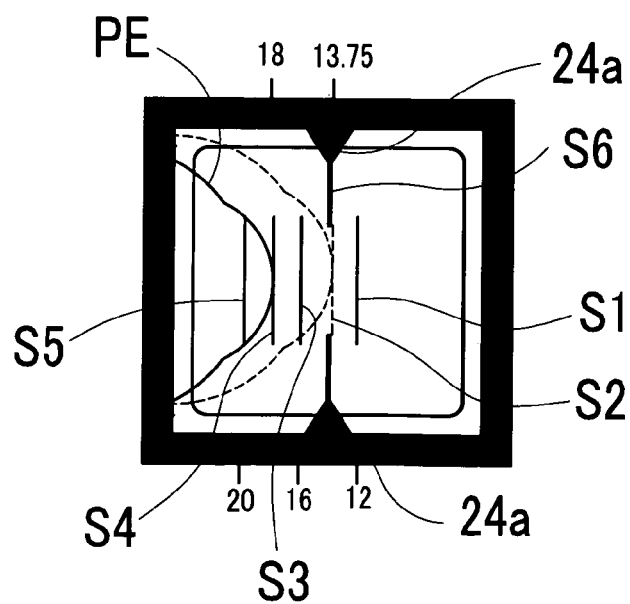
FIG. 4 is a view to explain the case that an examiner positions his eye in a point where an apex of a reticle appears aligned with a reference line and then a position of a corneal vertex of the examinee's eye is checked.

Thereafter, the examiner adjusts the position of his eye OE horizontally until the apexes of the reticles 24a appear aligned with the reference lines S6, as shown in FIG. 4, and then checks the position of the corneal vertex of the eye PE. If the eye PE has to be positioned to the point at a reference distance VD of 13.75 mm, the examiner moves a forehead rest not shown or the like to move the eye PE so that the corneal vertex appears to coincide with the scale line S2. If a person with sharply-chiseled features or a person with hollow eyes is examined, it is sometimes difficult to move his eye to the position at the reference distance. In this case, the examiner checks the position of the corneal vertex coincident with one of the other scale lines S1, S3 to S5 and determines the refractive power of the eye PE at the corresponding reference distance by using a predetermined conversion calculation based on the vertex distance VD.

Figure 5:
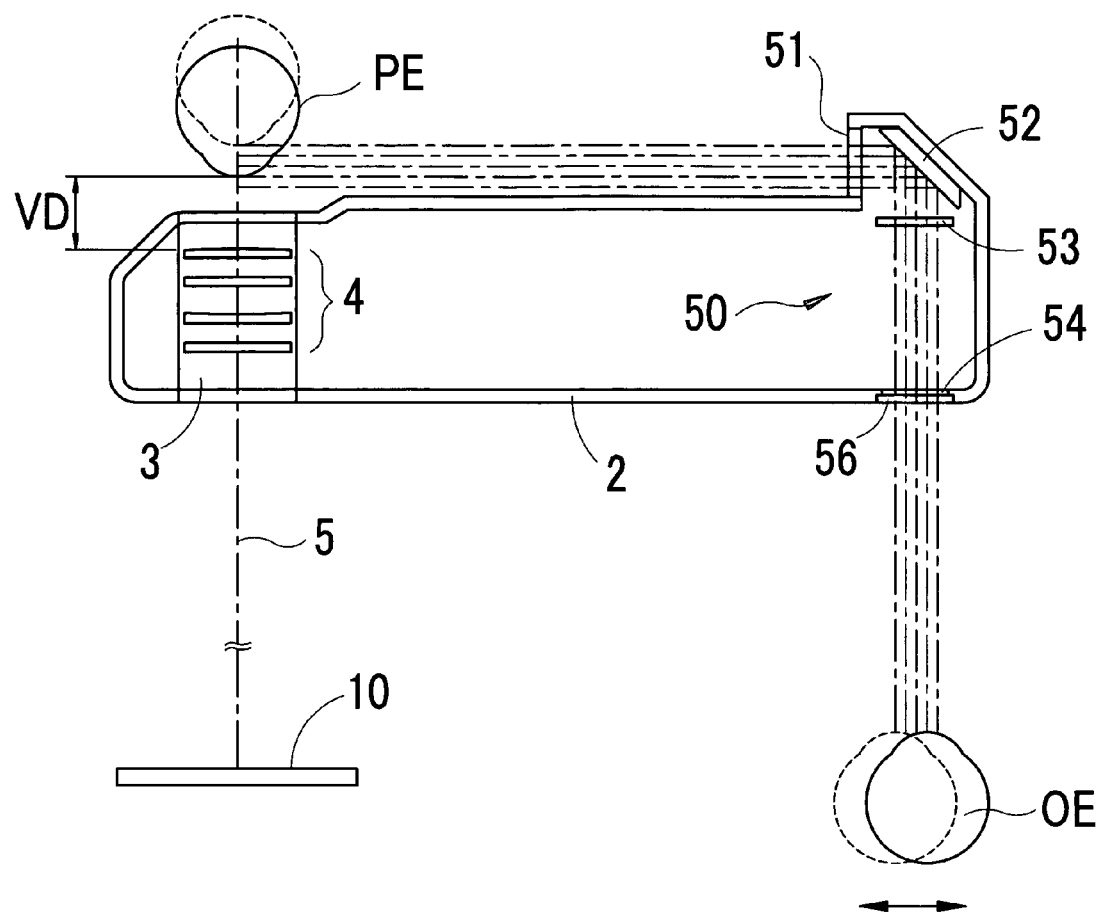
FIG. 5 is a schematic sectional view of an optometric apparatus in a second embodiment according to the present invention.

FIG. 5 is a schematic sectional view of an optometric apparatus in a second embodiment. In the present embodiment, like elements corresponding to those in the first embodiment are indicated by like numerals and therefore detailed explanations thereof are omitted. The apparatus in the present embodiment includes a cornea position alignment optical system 50 provided with a reflection mirror 52 mounted to be positioned at the side of the eye PE, a first aligning scale plate 53 placed on an optical path in a direction that the mirror 52 reflects light, and a second aligning scale plate 54. This second aligning scale plate 54 is mounted in an observation window 56 provided in the lens chamber unit 2 at the front side (which faces the examiner). The lens chamber unit 2 further includes a window 51 to be placed between the eye PE and the mirror 52. It is preferable that first aligning scale plate 53 and the second aligning scale plate 54 are placed as far away from each other as possible. The first aligning scale plate 53 may be mounted in the window 51 or between the window 51 and the mirror 52.

Figure 6A:
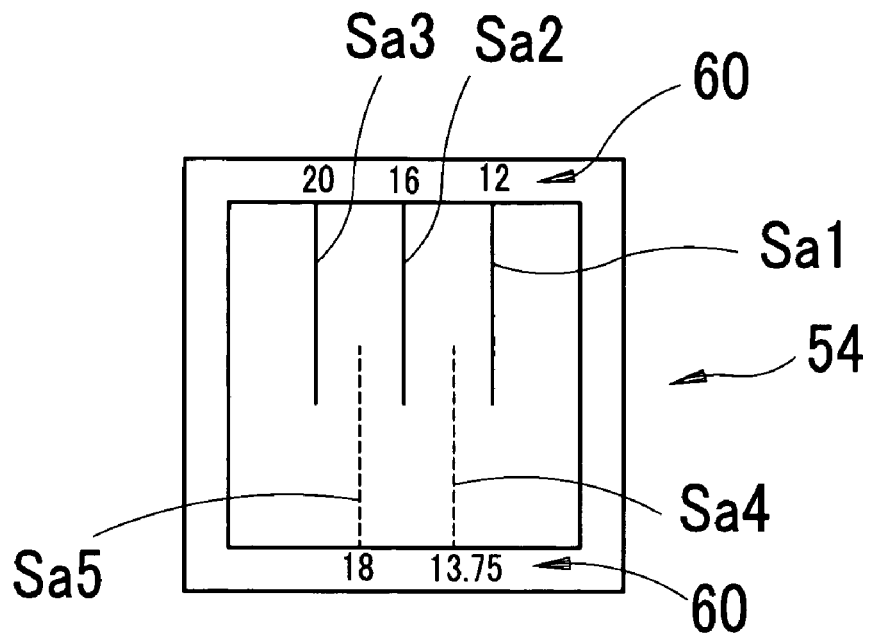
FIG. 6 is a schematic structural view of a second aligning scale plate and a first aligning scale plate.
Figure 6B:
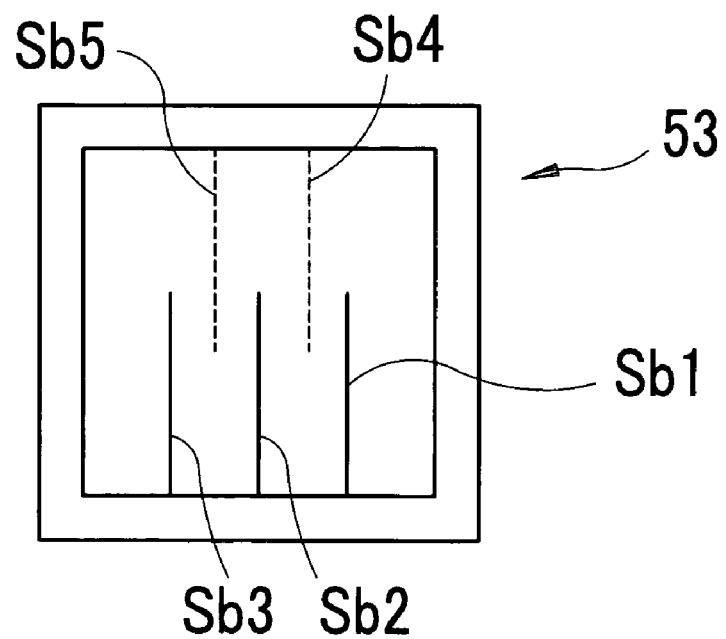
Figure 7:
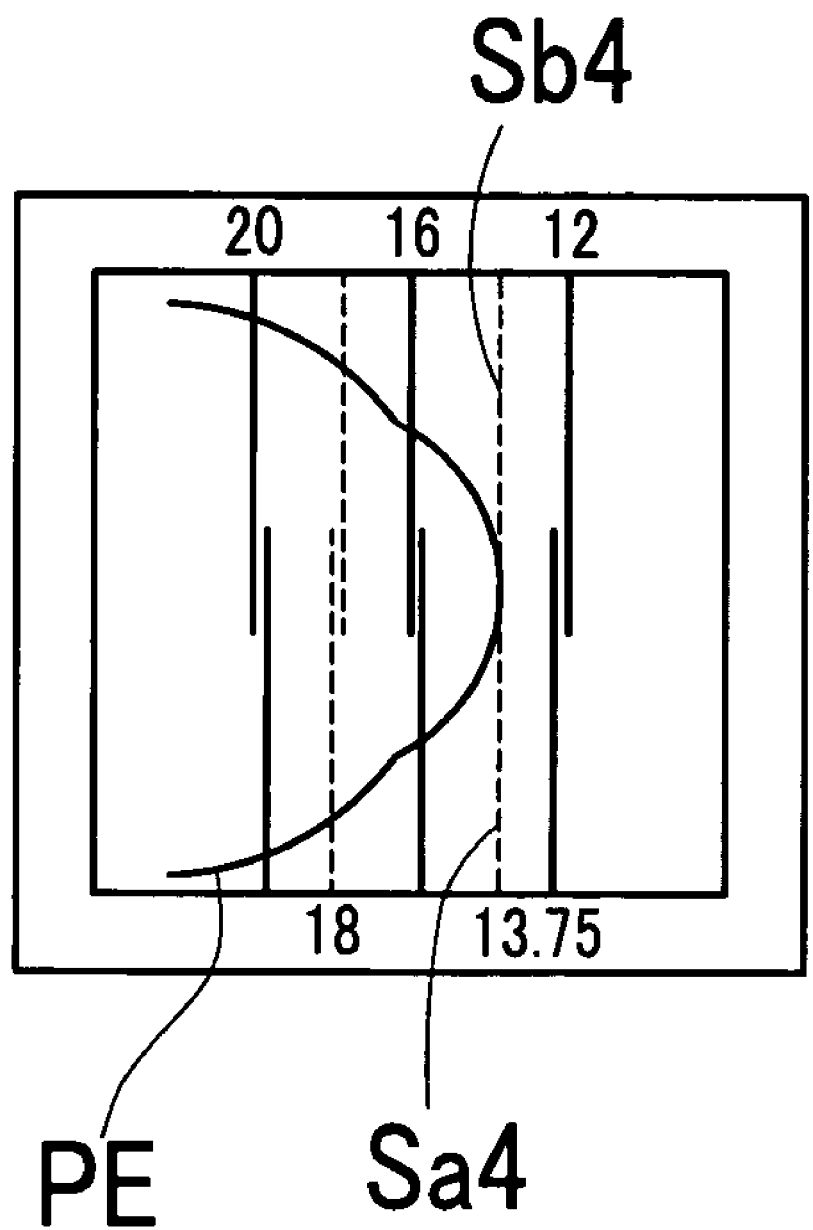
FIG. 7 is a view to explain the case that an examiner positions his eye in a point where a scale line Sa4 of the second aligning scale plate appears aligned, to be a single line, with a scale line Sb4 of the first aligning scale plate, and then a position of a corneal vertex of an examinee's eye is checked.
Figure 8:
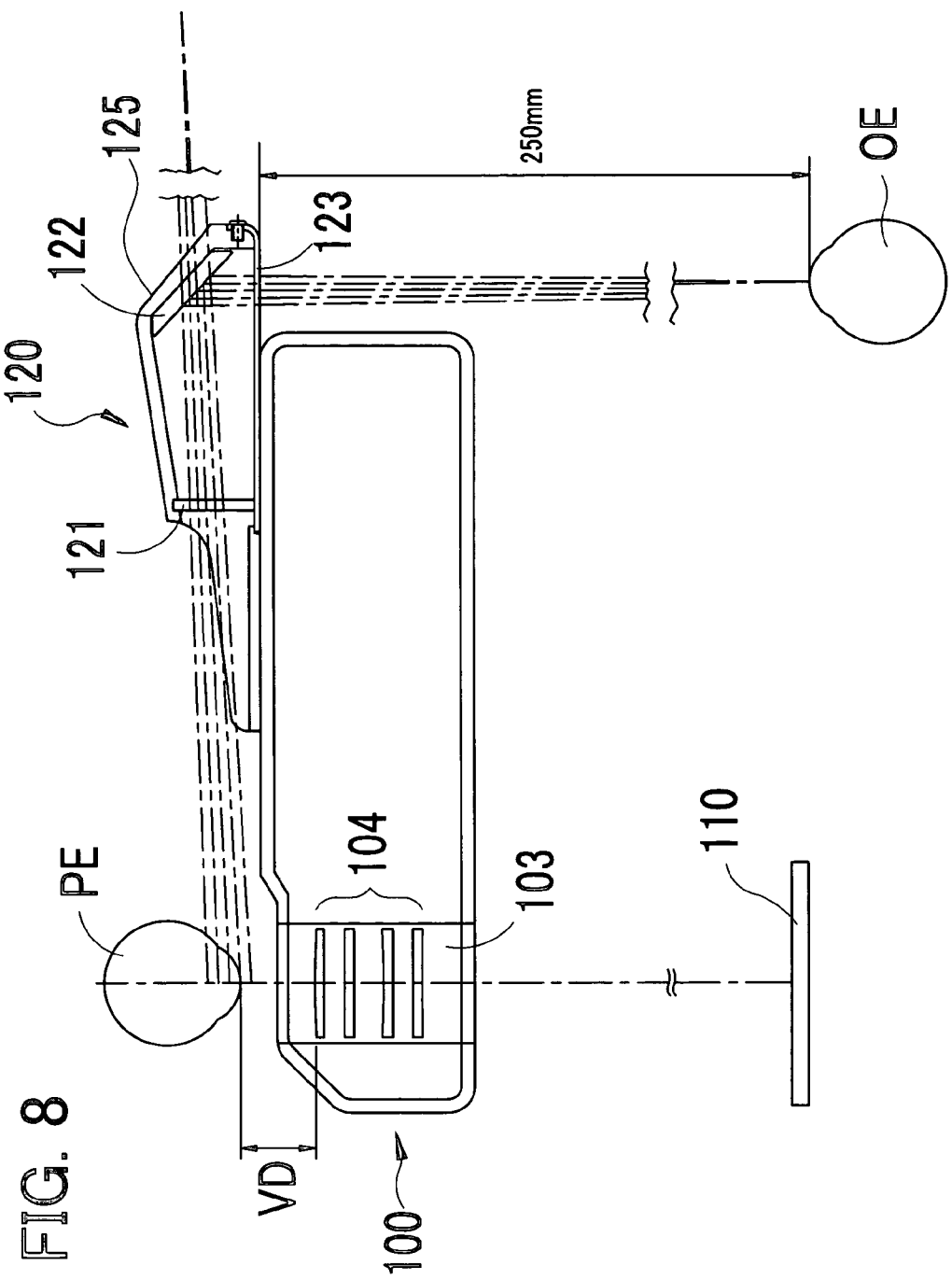
FIG. 8 is a schematic sectional view of a cornea position alignment optical system provided in a conventional optometric apparatus.
Figure 9:
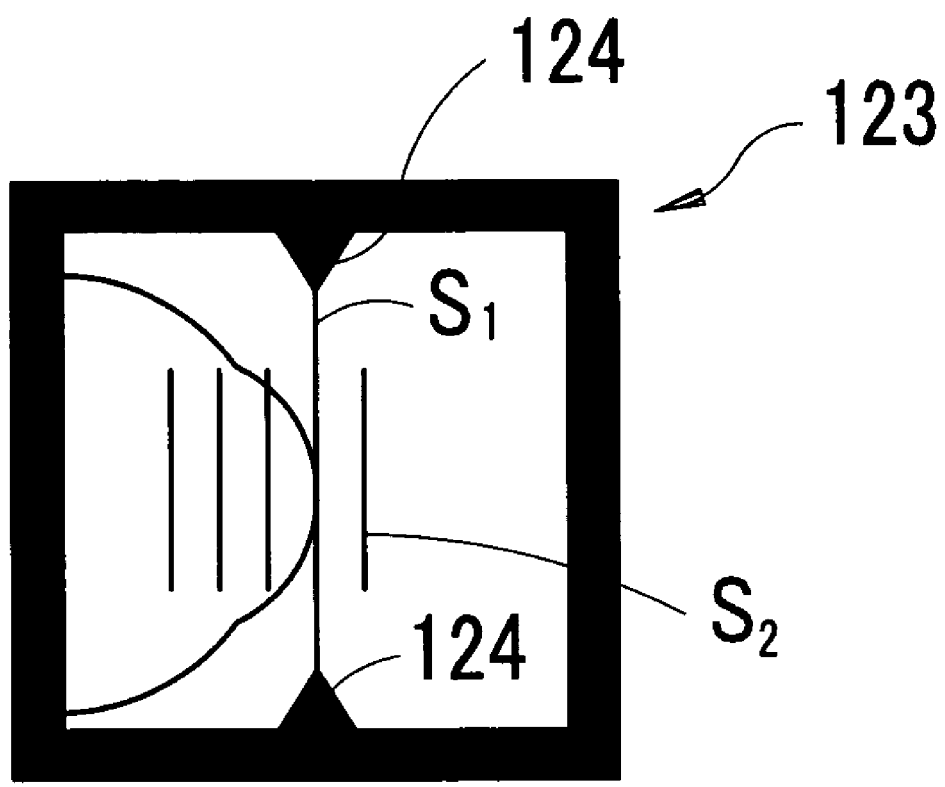
FIG. 9 is a view to explain the case that an examiner positions his eye in a point where a reticle of the reticle plate appears aligned with a long scale line S1 of the aligning scale plate, and then a position of a corneal vertex of an examinee's eye is checked.

FIG. 6A is a schematic structural view of the second aligning scale plate 54 and FIG. 6B is a schematic structural view of the first aligning scale plate 53. The first and second aligning scale plates 53 and 54 in the alignment optical system 50 are provided with reference marks different from those in the first embodiment to allow an examiner to position his eye OE at an arbitrary distance from the optometric apparatus. The first and second aligning scale plates 53 and 54 are each made of a transparent member formed thereon with a plurality of scale lines spaced at a predetermined distance pitch. In FIG. 6A, the second aligning scale plate 54 is provided with three solid scale lines Sa1, Sa2, and Sa3 each extending from an upper point to a point slightly below the center of the second aligning scale plate 54 and two dotted scale lines Sa4 and Sa5 each extending from a lower point to a point slightly above the center. The scale lines Sa1, Sa2, and Sa3 correspond to the vertex distances of 12 mm, 16 mm, and 20 mm, respectively. The scale lines Sa4 and Sa5 correspond to the vertex distances of 13.75 mm and 18 mm respectively. The intervals between the scale lines Sa1–Sa5 are determined to be equal to actual distance pitches. Near the scale lines Sa1–Sa5 there are marked numerical indices 60 representing the above vertex distances VD. Since the plurality of the scale lines corresponding to the vertex distances VD are formed so that the solid lines and the dotted lines are arranged alternately, the scale lines can be distinguished with ease.

The first aligning scale plate 53 is formed, as shown in FIG. 6B, with scale lines of which configuration is just inverted from the scale lines Sa1 to Sa5 formed on the second aligning scale plate 54. The scale lines of the first aligning scale plate 53 are three solid scale lines Sb1, Sb2, and Sb3 and two dotted scale lines Sb4 and Sb5. The scale lines Sb1, Sb2, and Sb3 correspond to the vertex distances of 12 mm, 16 mm, and 20 mm respectively. The scale lines Sb4 and Sb5 correspond to the vertex distances VD of 13.75 mm and 18 mm, respectively. The intervals between Sb1–Sb5 are also determined to be equal to actual distance pitches. The first and second aligning scale plates 53 and 54 may be formed with scale lines arranged completely identical to each other. However, these aligning scale plates 53 and 54 are preferably provided with scale lines arranged differently from each other, e.g., arranged in an inverted configuration as mentioned above, which makes it possible to easily check which vertex distance VD each scale line corresponds to. Alternatively, the aligning scale plates 53 and 54 may be constructed in different colors and different shapes.

A way to check the position of the corneal vertex of the eye PE through the use of the above structured alignment optical system 50 is explained below. The examiner peeps through the window 56 and moves his own eye OE in a horizontal direction so that the scale line of the second aligning scale plate 54 is adjusted to the corresponding scale line of the first aligning scale plate 53 for a desired vertex distance VD, and checks the position of the eye PE. To position the eye PE at the reference distance of 13.75 mm, for example, the examiner moves his own eye OE in the horizontal direction so that the scale line Sa4 of the second aligning scale plate 54 appears aligned with the scale line Sb4 of the first aligning scale plate 53. At this time, the other scale lines appear misaligned. The examiner then moves the forehead rest not shown so that the corneal vertex of the eye PE appears to coincide with the aligned scale lines Sa4 and Sb4. Thus, the eye PE can be positioned at the reference distance VD of 13.75 mm. If the eye PE can not be adjusted to the position at that reference distance VD, the examiner moves his own eye OE in the horizontal direction until the eye PE appears to coincide with the aligned ones among the scale lines of the first and second aligning scale plates 53 and 54 and reads the corresponding vertex distance VD at that time. Thus, the examiner can check the vertex distance VD of the eye PE.

In the above structured alignment optical system 50, the scale lines of the first and second aligning scale lines 53 and 54 are provided at actual distance pitches. Accordingly, the examiner is required only to move his own eye OE in the horizontal direction to check the position of the eye PE. Further, the examiner have only to position his eye OE at any distance at which he can easily see, without concern for the distance from the second aligning scale plate 54.

According to the present invention, as described above, the position of the examinee's eye can be accurately and easily checked.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optometric apparatus for subjectively examining visual functions of an eye of an examinee, the apparatus including:
 a disposing unit for disposing an optical element in front of the examinee's eye;
 a cornea position alignment optical system for checking a vertex distance between a back surface of the disposed optical element and a corneal vertex of the examinee's eye;
 wherein the alignment optical system includes an aligning scale plate provided with a scale for checking the vertex distance, a reticle plate provided with a reticle and placed in a different place from the aligning scale plate, and a first reference mark and a second reference mark for positioning an eye of an examiner in a point at a predetermined distance from the reticle plate, the first reference mark is provided to have a first positional relation with respect to the aligning scale plate and the reticle plate, the second reference mark is provided to have a second positional relation with respect to the aligning scale plate and the reticle plate, different from the first positional relation, the first and second reference marks appearing, to the examiner's eye, to have a predetermined positional relation with each other when the examiner's eye is positioned in the point at the predetermined distance from the reticle plate and views the reference marks from that point.

2. The optometric apparatus according to claim 1, wherein the first reference mark is formed on the aligning scale plate, and the second reference mark is formed on the reticle plate.

3. The optometric apparatus according to claim 1, wherein the first and second reference marks are each constructed of a rectangular frame-shaped line.

4. The optometric apparatus according to claim 1, wherein shapes and positions of the first and second reference marks are determined so that the reference marks appear overlapped, to the examiner's eye, when the examiner's eye is positioned in the point at the predetermined distance from the reticle and views the reference marks from that point.

5. The optometric apparatus according to claim 1, wherein the aligning scale plate has a mark for horizontal alignment of the examiner's eye with respect to the reticle.

6. An optometric apparatus for subjectively examining visual functions of an eye of an examinee, the apparatus including:
 a disposing unit for disposing an optical element in front of the examinee's eye; and
 a cornea position alignment optical system for checking a vertex distance between a back surface of the disposed optical element and a corneal vertex of the examinee's eye;
 wherein the alignment optical system is provided with a first aligning scale plate and a second aligning scale plate which are placed in different places and provided with a plurality of scales corresponding to vertex distances, the scales being arranged at actual distance pitches.

7. The optometric apparatus according to claim 6, wherein the plurality of scales are provided in different arrangements, different colors, or different shapes.

* * * * *